United States Patent [19]
Lingappa et al.

[11] Patent Number: 4,983,521
[45] Date of Patent: Jan. 8, 1991

[54] TRANSMEMBRANE INTEGRATOR SEQUENCES

[75] Inventors: Vishwanath R. Lingappa, San Francisco, Calif.; Charles S. Yost, Pittsburgh, Pa.

[73] Assignee: The Regents of the University of California, Oakland, Calif.

[21] Appl. No.: 906,809

[22] Filed: Sep. 12, 1986

Related U.S. Application Data

[63] Continuation-in-part of Ser. No. 545,727, Oct. 26, 1983, abandoned.

[51] Int. Cl.$^5$ .................. C12P 21/00; C12N 15/00
[52] U.S. Cl. .......................... 435/172.3; 435/172.1; 435/68.1; 435/69.1; 435/188; 435/69.8; 435/711; 935/47; 935/48; 935/49
[58] Field of Search .................. 435/68, 69, 70, 172.3, 435/188, 272

[56] References Cited
PUBLICATIONS

Silhavy, T. J. (1977) PNAS 74:5411–5415.
Moreno et al., Nature 286:356 (1980).
Bassford et al., J. Bacteriol 139:19 (1979).
Talmadge et al., Nature 294:176 (1981).
Sabatini et al., J. Cell Biology 92:1–22 (1982).
Lingappa et al., Nature 281:117 (1979).

*Primary Examiner*—Richard A. Schwartz
*Assistant Examiner*—Anne Brown
*Attorney, Agent, or Firm*—Bertram I. Rowland

[57] ABSTRACT

Novel DNA constructions are provided, as well as their expression products, involving the use of transmembrane integrator sequences joined from one to two open reading frames and optionally a signal sequence, particularly at the N-terminus. The DNA constructs when used with membranal translation systems provide for translocation of the peptides into the membrane. Alternatively, a signal sequence may be introduced internal to an open reading frame, where the resulting translation product may be processed by a membrane to provide two peptides.

19 Claims, 3 Drawing Sheets

TRANSMEMBRANE INTEGRATOR SEQUENCES

CROSS REFERENCE TO RELATED APPLICATIONS

The application is a continuation in part of application Ser. No. 545,727, filed Oct. 26, 1983, now abandoned as of the filing date of the subject application.

BACKGROUND OF THE INVENTION

1. Field of the Invention

Cellular membranes are dynamic structures, where proteins are frequently capable of moving in the plane of the membrane, but remain non-covalently bound to the membrane. The membrane proteins serve a wide variety of functions, providing for host recognition, processing of polypeptides, transport of inorganic and organic compounds across the membrane barrier, ion and energy pumps, and the like. The membrane proteins are essential for the viability of the cell.

The membrane proteins which are external to the cell can frequently act as receptors, binding to a wide variety of ligands. Such receptors can be involved in the predisposition to disease, host specificity for viral infection or immunity, activation of intracellular enzymes, or other essential cellular function.

The plasma membrane proteins assume a variety spatial relationships with the membranes. The protein can extend from either or both faces of the membrane, extending into the cytoplasm or into the external medium. The membrane protein may extend only once through the membrane or extend a multiplicity of time through the membrane.

One of the mysteries which is presently being unraveled is how a cell designates the location to which a particular polypeptide product is to be directed. The ability to direct particular polypeptides to a particular cellular site can have far ranging consequences for the cellular production of a wide variety of organic products of interest, for use in the diagnosis and treatment of disease, and for the understanding of cellular functions and responses to various ligands.

2. Description of the Prior Art

Anderson et al., *J. Cell Biology* (1982) 93:501 report that both secretory and integral transmembrane protein (ITMP) signal sequences are recognized by common signal recognition elements. Blobel, *Proc. Nat.. Acad. Sci. USA* (1980) 77:1496 postulates a mechanism for intracellular protein topogenesis. Early et. al., *Cell* (1980) 20:313; Rogers et al. *Cell* (1980) 20:303; as well as others, describe the DNA and protein sequences and genomic DNA exon structure of the IgM heavy chain. Lingappa et al., *Proc. Natl. Acad. Sci. USA* (1977) 74:2432 describe a cell-free transcription-linked translocation-coupled translation system with native secretory protein mRNAs. Katz et al., ibid. (1977) 74:3278 describe the same system for membrane mRNAs. Lodish et al., *Int. Rev. Cytol. Supp.* (1981) 12:247 postulated that the extreme carboxy terminus of an ITMP serves as a passive "anchor" to retain an already completed chain in the membrane. Engleman and Steitz, *Cell*(1981) 23:411–422 hypothesized that translocation was mediated exclusively by the hydrophobic-polar helical hairpin of a nascent chain interacting with the lipid bilayer. The plasmid pU6 is described by Rogers et al, *Cell* (1980) 20:303. The use of dog pancreas microsomal membranes with the cell-free system described above is described by Muller et al., *J. Biol. Chem.* (1982) 257:11860–11863. Fusion proteins between secretory and cytosolic proteins are described by Moreno et al., *Nature* (1980) 286:356. Conversion of ITMPs into secretory proteins by carrying out deletions of carboxy transmembrane segments is described by Boeke and Model, *Proc. Natl. Acad. Sci. USA*. (1982) 79:5200; Gething and Sambrook, *Nature* (1982) 300:598; Kondor-Koch et al.. *Proc. Natl. Acad. Sci. USA* (1982) 79:4525 and Rose and Bergmann, *Cell* (1982) 30:753. Perara and Lingappa (1980) *J. Cell Biology*, 101:2292–2301 and Perara, et al. (1986) *Science* 232:348–352 describe positional varying of a signal sequence and the effect of structural gene termination on peptide translocation, which disclosures are incorporated herein by reference.

SUMMARY OF THE INVENTION

DNA constructs, expression vectors and methods are provided for introducing hybrid peptides into membranes. By appropriate choice of signal sequences the peptide may extend from either or both surfaces of the membrane. The hybrid constructs employ a transmembrane integration sequence in conjunction with a sequence other than the wild-type sequence joined to the transmembrane integrator sequence. Cells modified with the hybrid peptides find a variety of uses in vaccines, in assays, and in modifying cellular properties.

DESCRIPTION OF SPECIFIC EMBODIMENTS

Figure 1:
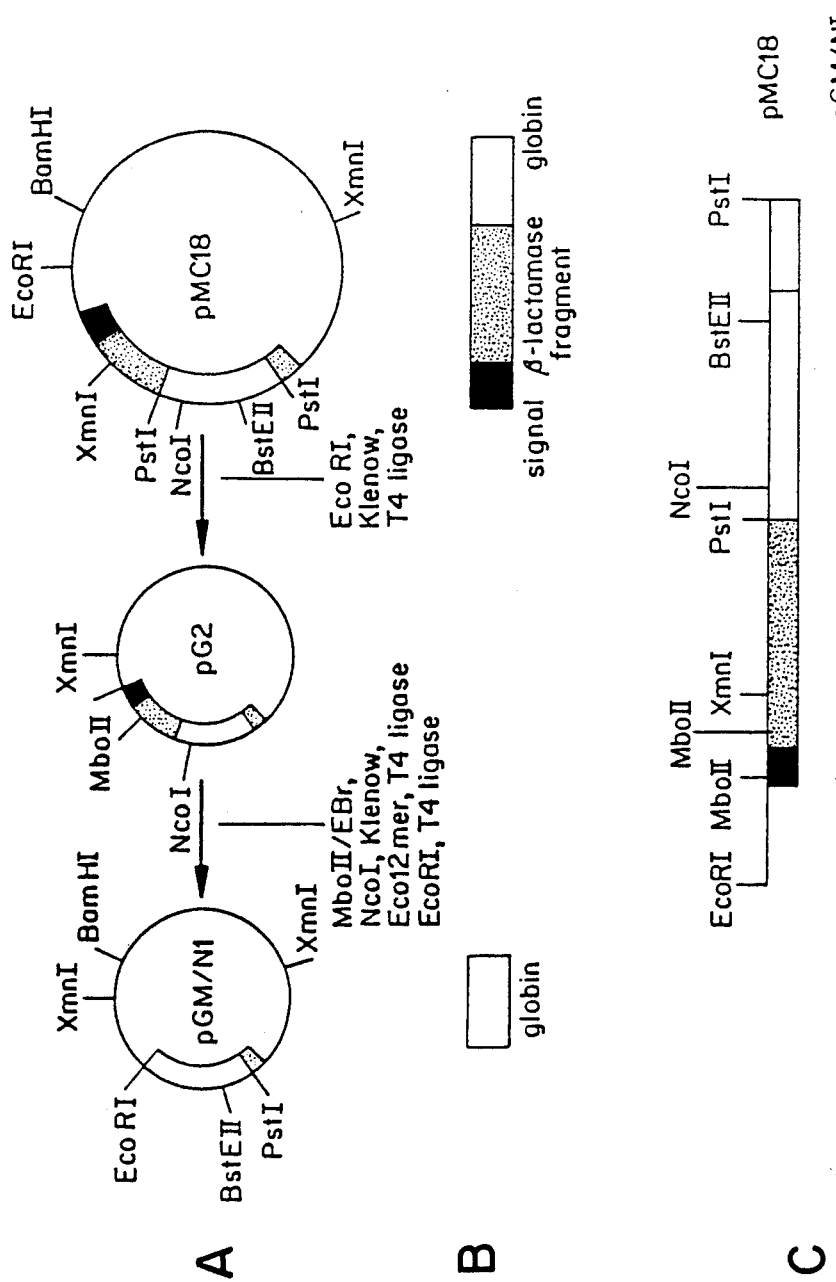
FIG. 1 is a flow diagram of the preparation of plasmids pGM/N1.

Methods and compositions are provided for the non-covalent binding of poly(amino acids) (includes polypeptides and proteins, including prosthetic groups) to a cellular membrane. DNA constructions are introduced into a cellular host under conditions providing for expression, whereby a poly(amino acid) is produced having topogenic transfer signals, which signals may be interrupted by and/or followed by DNA coding sequences encoding polypeptides of interest in reading frame with the signals, where the end result is the non-covalent stable binding of the protein to a cellular membrane. The membrane of the cell is modified from the parent or wild-type cell, through a process usually initially involving the endoplasmic reticulum and translocation to a different membrane of the cellular host.

The topogenic sequences are DNA sequences, usually involving at least about 10 codons and fewer than about 100 codons, which direct whether a nasent polypeptide will translocate in relation to the endoplasmic reticulum or microsomal membrane and be non-covalently bound to the membrane. The topogenic sequences may be divided into signal sequences which serve as a translocator sequence which may be terminal or internal to the open reading frame, and determine the translocation of the polypeptide chain across the membrane and transmembrane integration sequences which can determine whether the polypeptide partially traverses the membrane remaining bound to the membrane rather than being completely transferred across the membrane.

Where the topogenic signal sequence is terminal and followed by a processing signal—usually two or more codons recognized by a peptidase for proteolytic cleavage—the signal sequence will normally be removed upon translocation. Where the signal sequence is internal, it will normally be retained by the N-terminal protein, but the C-terminal sequence will be cleaved from the signal sequence.

The transmembrane integration sequence or stop sequence serves to stop the translocation of itself across the membrane, resulting in the peptide remaining bound to the membrane.

By appropriate combinations of DNA sequences in open reading frame involving combinations of signal sequences, transmembrane integration sequences and coding sequences for polypeptide regions of interest, a polypeptide may be oriented in conjunction with a membrane so as to have one or more regions on one or both sides of the membrane layer.

The first topogenic sequence to be considered is the signal sequence. Where the signal sequence is at the 5'-end (N-terminus) of the structural gene, it will be referred to as the start transfer signal sequence.

The start transfer signal may be naturally present with the polypeptide of interest or may be added, depending upon whether the polypeptide of interest is naturally translocated through the membrane, e.g. secretory, or a non secretory polypeptide, e.g. cytoplasmic, as well as the nature of the host and whether the signal sequence is functional in the host. The start transfer signal may serve as a secretory signal, optimally associated with a processing signal, which signal sequence directs the translocation to a cellular membrane and, in the presence of the processing signal, will normally be cleaved by a peptidase, so as to be absent from the final product.

The internal signal sequence may be naturally present with the peptide coding sequences, but will usually be introduced by ligation, in vitro mutagenesis, or the like. Depending upon the presence or absence of a processing signal, the signal leader sequence may be processed so as to provide one or more membrane proteins, which proteins may include all or only a portion of the expressed peptide produced.

The transmembrane integration sequence may be obtained from membrane bound proteins, being that sequence which crosses the membrane at least in part and is non-covalently retained in the membrane. The transmembrane integration sequence which is employed in the construct may terminate with the polar domains or may include flanking regions. The polypeptide(s) of interest may extend from either or both surface of the membrane.

The signal sequence construct will usually encode a pre-poly(amino acid). That is, in most instances processing signals will be present downstream from the signal sequence separating the signal sequence from the next domain, either the stop signal or a structural gene encoding a polypeptide of interest. In the presence of an appropriate cellular membrane, the pre-poly(amino acid) is processed to the mature poly(amino acid).

The presence of novel polypeptides bound to the cellular membrane can provide for a variety of new functions for the cell, enhance existing functions, or provide novel cells which can be used in the diagnosis and therapy of diseases.

The constructs will usually be joined to other functional sequences to provide for extra-chromosomal replication or integration, so as to be maintained in the progeny of transformed cells. Thus, clones of cells may be achieved whose properties have been modified by virtue of having novel polypeptides external or internal to the cell. The poly(amino acids) which become bound to the membrane surface will be referred to as integral transmembrane proteins ("ITMPs"). These polypeptides may be naturally occurring, synthetic, or combinations thereof. The portions of the poly(amino acid) extending from the membrane may be portions of a single naturally existing protein, may be different proteins or may be the same protein. In some instances, the ITMP may be a naturally occurring ITMP which is introduced into a foreign host and supplied with a start transfer signal recognized by the foreign host. For the most part, the ITMP will be a novel poly(amino acid) not normally bound to the membrane, which is joined to all or a portion of the transmembrane integrator of a different naturally occurring polypeptide.

The constructs of the subject invention containing a transmembrane integration sequence and encoding for the hovel poly(amino acids) will for the most part have the following formula:

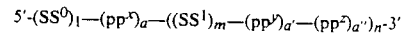

wherein:

The 5' and 3' intends the ends of the coding strand;

ss intends the signal sequence which involves signals, two or more codons coding for an amino acid sequence recognized by a peptidase which cleaves at the processing signal to separate the C-terminal peptide from the polypeptide encoded by the signal sequence; the signal sequence may be at a terminus, particularly the 5'-terminus or may be internal to the sequence as indicated in the formula; the signal sequence may be endogenous or exogenous to the host, and depending upon the position of the signal sequence and the presence or absence of a processing signal, may be retained with all or a portion of the peptide encoded by the open reading frame(s) included in the construct; the 0 and 1 intend that the signal sequences may be the same or different, so that there may be one or more signal sequences involved in the construct;

pp intends an open reading frame, in reading frame with the upstream signal sequence and coding for a peptide sequence of interest;

the letters x, y, and z intend that the various sequences encoding the polypeptides may be the same or different; each open reading frame will include at least one codon and may have 500 codons or more, usually having fewer than about 300 codons, more usually having fewer than about 250 codons;

l and m are the same or different and are 0 or 1;

a, a' and a" are the same or different and are 0 or 1, at least one of a, a' or a" being 1;

tmi intends a sequence having a plurality of codons, usually at least 10 and generally not more than about 100, more usually not more than about 50, frequently not more than about 30, which codes for the transmembrane integrator sequence;

n is at least 1 and generally does not exceed about 10, more usually not exceeding about 6, frequently not exceeding about 2 and more frequently being equal to 1.

The transmembrane integrator sequence will generally be characterized by codons expressing a hydrophobic region of at least about 10 amino acids, and usually not more than about 90 amino acids, more usually not more than about 40 amino acids flanked by short polar regions of from about 1 to 10, usually 1 to 5, more usually 2 to 5 amino acids, with a majority of amino acids, frequently all of the amino acids being polar, particularly a fraction of the polar amino acids being cationic.

The transmembrane integrator sequence may be obtained from a variety of genes where the wild type peptide traverses the membrane one or more times. The various topogenic sequences may be obtained from wild-type genes, be synthesized copies thereof, mutations or modifications thereof, so long as the function is retained. The topogenic sequences may be from the same or related host as the host in which the construct is expressed or an unrelated host, since there appears to be substantial interspecies recognition of the sequences.

The start transfer signal sequence may provide for a "pre" peptide where the signal sequence is followed by a processing signal, so that the start transfer sequence is cleaved to leave the mature peptide bound to the membrane. By using combinations of tropogenic sequences various spatial orientations may be achieved with an intact cellular or microsomal membrane. One or both (amino and carboxy) termini may be in the cytoplasm or in the external medium. There may be a single or multiple peptide domains in the cytoplasm and/or external medium. The domains may be the same or different depending upon the purpose for which the peptide is bound to the membranes. For example, by having an N-terminal signal sequence and an internal transmembrane integrator sequence, the N-terminus may extend from the opposite face of the membrane translation system, e.g., microsome, cell or the like, or be internal to the membrane enclosed system, with the C-terminus in the cytoplasm or external to the membrane enclosed system. With only an internal transmembrane integrator sequence, both N- and C-termini may be external to the cell or internal to the microsome. By having a signal sequence and a plurality of transmembrane integrator sequences separated by open reading frames, the polyamino acid may be threaded through the membrane, so as to have a plurality of domains appearing on one side or the other side of the membrane.

The construct described above may be used by itself or may be litigated to a wide variety of DNA sequences having a variety of functions. Thus, depending upon whether integration or extrachromosomal maintenance is desired, different flanking regions may be employed. For integration, integration may involve legitimate or illegitimate recombination. The flanking regions may involve sequences homologous with DNA sequences of the host, which sequences may extend for at least about 20 bp to 500 bp or more.

Flanking regions may include insertion sequences, including terminal repeats and inverted repeats, as found with transposons, viruses and the like. In addition, the flanking region may include one or more autonomously replicating segments (ars) which allow for enhanced maintenance in the cell. In addition to the ars, the flanking regions may include one or more markers which allow for selection to enhance the probability of integration into the genome or stable maintenance through repeated passages of the construct as an extrachromosomal element. Finally, there are various plasmids which are tumorigenic, having DNA sequences which insert themselves into eukaryotic genomes. Illustrative of such plasmids are the Ti and Ri plasmids, which become inserted into the genome of plant cells. The T region of the Ti plasmid would then serve as a flanking region for the construct.

Alternatively, one can provide for the stable maintenance of a wide variety of extrachromosomal elements in a wide variety of hosts. The extrachromosomal elements may be derived from plasmids, phage, viruses, and chromosomes, by employing, for example, in combination the centromere (CEN) and an ars.

Where an extrachromosomal element is employed, there will usually be other functional sequences, particularly markers, which allow for selection. Conveniently, markers may involve providing prototrophy to an auxotrophic host, resistance to a cytotoxic agent, e.g. antibiotics, heavy metals, toxins, such as colicins, or the like, or immunity from virus.

For the most part, these constructions will have the following formula, where outside the construct as defined in the previous formula the order indicated is mostly arbitrary and is not necessary for the maintenance and viability of the extrachromosomal element. It should be further understood that the extrachromosomal element may be linear or circular, depending upon the nature of the replication system. Furthermore, a DNA sequence encoding for a retrovirus may be employed, where the isolated sequence may be RNA and single stranded to DNA as the replicative form (RF).

The following formula indicates in a general way the extrachromosomal constructs:

$$(rep.s)_b - M_c - t.i. - tr.i. - \text{"construct"} - tr.t. - t.t. -$$

wherein:

"construct" intends: $5'-(SS^0)_1-(pp^x)_a-((SS^1)_m-(pp^y)_{a'}-(pp^z)_{a''})_n-3'$, where all the symbols have been defined previously;

t.i. intends transcriptional initiation and regulatory sequences, which may include one or more promoters, enhancers, operators, activators, RNA polymerase binding site, 'TATA' sequence, cap sequence, 'CAAT' sequence, or other sequence associated with transcriptional initiation;

tr.i. intends translational initiation signals, such as a ribosomal binding site, initiation codon, or other sequence involved with translational initiation;

tr.t. intends translational termination signals which involve one or more stop codons;

t.t. intends transcriptional termination signals which will be downstream from the construct, usually from about 1 to 200 bases downstream from the construct and will include a terminator, usually a polyadenylating sequence, or other sequences associated with transcriptional termination;

rep.s. intends a replication system, wherein b is an integer of at least 1 indicating that there may be present more than one replication system, where the different replication systems may involve replication systems having different properties, such as temperature sensitivity, runaway replication system systems, partial replication systems, e.g. COS type systems, etc.;

M intends a marker as described above, wherein c may be 0, but usually is an integer of at least 1, indicating that there may be one or more markers, where the markers may differ as to their properties, as to the recognition by different hosts, or the like; the hyphens in the above formula indicate that there may be non-coding sequences, generally there will be noncoding sequences, separating the various functions.

Furthermore, in addition to the above-indicated sequences, further sequences may be included, such as additional enhancers, additional promoters, which are in tandem with or a substitute for the promoter associated with the 5'-sequence signal, additional terminators, or the like. Conveniently, shuttle vectors may be employed having two replication systems, where one replication system is employed for cloning in prokaryotes and the other replication system provides for the maintenance of the extrachromosomal element in an expression host.

The transmembrane integrator or the stop transfer sequence (tmi) may be obtained from any convenient source, either prokaryotic or eukaryotic. Illustrative sources include membrane immunoglobulins bound to the membrane, e.g. mIgM, mIgG, etc., Thy-1, the antigens of the major histocompatibility complex (MHC), T-cell antigen receptor, transport proteins, ion channels, membrane receptors, outer membrane proteins, viral envelope proteins, and the like. The tmi sequence, will be characterized by having a highly polar region followed by a highly non-polar region, usually followed by another highly polar region. Generally, one of the highly polar regions will have from about 3 to 15, more usually from about 6 to 15 amino acids of which at least about 40% by number, more usually at least about 50% by number, will be charged polar amino acids. By charged polar amino acids is intended an amino acid containing a carboxy group or amino group, where the charged polar sequence will generally have greater than about 50% of the polar amino acids of the same charge type, more usually greater than about 70 number percent of the amino acids of the same charge type. The other of the hydrophilic regions may have from 1 to 15, usually 1 to 10 amino acids, with at least one amino acid being charged.

Particularly, the N-terminus of the amino acid stop sequence will be preferably negatively charged, that is, having carboxy amino acids, while the C-terminus will be positively charged, that is, having positive amino acids. The negative amino acids include glutamic acid and aspartic acid, while the positive amino acids include particularly lysine and arginine, as well as histidine.

The hydrophobic region will have a plurality of amino acids free of any polar substituent, that is, amino acids such as glycine, alanine, valine, leucine, isoleucine, and the like. Other substantially hydrophobic amino acids include tryptophan, methionine, etc. Usually, there will be fewer than 25%, more usually fewer than 20% of the amino acids in the hydrophobic region, which are polar amino acids as defined above.

The signal sequence will have certain similarities to the tmi sequence. The signal sequence at the N-terminus or internal will be the secretory signal and will normally include processing signals, which allow for membrane bound enzymes or other peptidases to remove the secretory signal sequence, so that the amino terminus which is extracellular will be internal to the sequence encoded for by the construct and free of the signal sequence.

The signal sequence will have a hydrophobic region, usually preceded by one or more hydrophilic amino acids and terminating in a polar region, which polar region involves the processing signal. The processing signal may involve one or more basic polar amino acids, namely lysine and arginine, usually one to two polar amino acids. Alternatively, dipeptides involving X-Ala may also serve as a processing signal.

The hydrophobic region will usually involve at least about 10 amino acids, and not more than about 50 amino acids, having fewer than 25 number percent, usually fewer than 20 number percent charged polar amino acids, having free carboxy or amino groups. Signal sequences and processing signals may be derived from a wide variety of sources, both prokaryotic and eukaryotic, such as the proteins described previously, as well as secreted proteins, such as α-factor, a-factor, β-lactamase, amylase, etc. See also U.S. Pat. Nos. 4,336,336 and 4,338,397.

The signal sequences will vary widely, depending upon the particular nature of the polypeptide to be secreted. Desirably, signal sequences should be chosen, not only by virtue of the host from which they are obtained, but also by the nature of the polypeptide which is naturally secreted. Desirably, one would wish to have the polypeptide following the signal sequence of a similar nature to the naturally occurring polypeptide associated with the signal sequence.

In preparing the constructs of the subject invention, a wide variety of techniques may be employed, depending upon the construct of interest, the materials available for use, the need to isolate a previously unidentified cDNA or genomic DNA to provide a sequence encoding the polypeptide of interest, or in the case of short polypeptides, the opportunity to synthesize in whole or in part the short polypeptide. Thus, only very general rules can be suggested, which can be used in light of the working exemplification.

At this time and at an ever expanding rate, a greater variety of vectors are available to provide replication systems, for eukaryotic and prokaryotic cells, as well as combinations thereof. These vectors will normally have markers for hosts which recognize the replication system(s) which are present in the vector. The markers have been described previously.

In addition, the vector will normally have one or more unique restriction sites for insertion of a DNA sequence into the vector. These sites may involve insertion into a marker, so that selection involves the loss of a phenotypic property. Vectors which are used solely for cloning will not require the presence of transcriptional regulatory signals. However, there are now available a large number of expression vectors, which have convenient sites for insertion of a structural gene encoding for a polypeptide of interest, where the site is intermediate the transcriptional initiation and termination signals. The transcriptional initiation signals may include one or more promoters, one or more enhancers, TATA box, CAAT signal, cap signal or other sequence or base pair which enhances promoter efficiency. Furthermore, various specialized transcriptional regulatory sequences can be employed, such as temperature sensitive promoters, operators, activators, etc. For termination, there should be a terminator which acts efficiently with the promoter(s), usually there will be a polyadenylation sequence and in some situations, stop codons may be associated with the terminator.

For translation, there may be present a ribosomal binding site and any other associated sequences associated with the translation, as well as one or more stop codons at the end of the coding sequence of the structural gene.

Where a vector is available which has the necessary regulatory sequences, but does not have a convenient restriction site, which can be joined to the polynucleotide sequence, various techniques allow for modification of the structural gene and/or the vector. Linkers and adapters can be used, the restriction site may be changed, so as to provide for a different recognition sequence, or the vector may be modified by in vitro mutagenesis, resection, repair and linker ligation, or the like, to allow for the proper insertion of the structural gene.

In some situations, vectors can be prepared which have signal sequences and processing signals, allowing for the insertion in frame with the signal sequence and processing signal, where a restriction site is provided internal to the signal sequence or processing signal. Thus, by employing an adapter, one can join the adapter to the structural gene, which adapter provides for the missing bases of the signal sequence or processing signal. In many instances, conservative mutations may be made for the signal sequence and/or processing signal to introduce a convenient restriction site.

Where a vector having the desired properties is not available, one can employ the experience taught in the literature for isolating and assembling the various different sequences to provide for a functioning construct.

Once the construct is prepared, it may be used for transcription and translation. Expression can be achieved in vitro using a cellular membrane containing lysate (Muller et al. (1982) supra) or by introducing the construct into a cell. The manner in which the cell is modified will depend to some degree on the vector and may include transformation employing calcium precipitated DNA, transfection, conjugation, or the like. The modified cells may then be grown in an appropriate nutrient medium and modified cells selected by means of one or more markers present on the construct. In this manner modified cells are obtained with novel poly(amino acids) having polypeptides extending intra- and/or extracellularly from a membrane, e.g. the plasma membrane. The subject method provides, therefore, means for translocating a poly(amino acid) to a membrane, where the poly(amino acid) is noncovalently bound to the membrane. The poly(amino acid) is translocated in a manner which has the N-terminus extracellular.

By appropriate use of the tmi by itself, used singly or multiply, where each tmi is separated by an open reading frame, or in conjunction with a signal sequence, a variety of different conformations may be achieved between the poly(amino acid) encoded by the construct and the membrane. By using a combination of a signal sequence and a tmi at the N-terminus, the poly(amino acid) may be retained in the cytoplasm. By having the signal sequence and tmi separated by a first poly(amino acid) sequence and the tmi followed by a second poly(amino acid) sequence, the first poly(amino acid) sequence will be extracellular and the second poly(amino acid) sequence will be intracellular. By having a tmi internal to a poly(amino acid) sequence, both the N- and C-termini may be extracellular. By having a plurality of spaced apart tmi sequences in conjunction with a signal sequence, the poly(amino acid) domains flanked by the tmi's may be threaded through the membrane to have alternating poly(amino acid) domains on opposite sides of the membranes.

Both prokaryotic and eukaryotic cells may be modified. Such cells include bacteria, algae, fungi, filamentous fungi, non-vertebrate cells, fish cells, mammalian cells, primate cells, human cells, etc.

The subject invention can be used in the preparation of vaccines where prokaryotes are modified to have membrane proteins of other species presented in the prokaryotic cell surface. In this way, a nonpathogenic prokaryotic host may be modified to produce an immune response to one or more viral or cellular pathogens, where the protein is in a natural membrane setting.

A wide variety of ITMPs can be prepared having functions other than vaccines. For example, a naturally occurring ITMP can be selected which has a receptor and an internal portion. Upon binding of the receptor to an homologous ligand, an intracellular process is initiated. By isolating the DNA sequence encoding for the signal sequence containing precursor to the ITMP, the DNA sequence encoding the extracellular polypeptide may be replaced with a sequence encoding for a different receptor. In this manner the intracellular process may be initiated with a ligand different from the natural ligand.

ITMPs may also be used as markers for cells. By combining a construct according to the present invention with a structural gene of interest, transformed cells may be isolated by affinity chromatography.

Stem cells may be modified with ITMPs to modify, enhance or inhibit suppressor, helper or killer functions.

Cells may be modified to provide for surface receptors or ligands for use in in vitro diagnostic assays, in vitro diagnosis, or for therapy. The presence of the novel ITMPs permits the targeting of proteins to specific intracellular compartments or to particular cells, cells of organs, and the modification or cells to provide altered spectra and kinetics of action, half-life and clearance.

The following examples are offered by way of illustration and not by way of limitation:

EXPERIMENTAL

Example I

All restriction endonucleases, nuclease Bal 31, calf intestinal alkaline phosphatase, SP6 RNA polymerase, T4 DNA ligase, and Klenow fragment of *E. coli* DNA polymerase were obtained from Boehringer Mannheim Diagnostics, Inc., Houston, Tex. or from New England BioLabs, Beverly, Mass. RNase inhibitor was from Promega Biotex, Madison Wis. Staphylococcal protein A-Sepharose was from Pharmacia, Inc., Piscataway, N.J. Rabbit anti-bovine prolactin was from United States Biochemical Corp., Cleveland, Ohio. Proteinase K was obtained from Merck, FRG; endoglycosidase H and [$^{35}$S]-methionine (translation grade, >800 Ci/mmol) from New England Nuclear, Boston, Mass.; Nikkol (octaethyleneglycol-mono-n-dodecyl ether, a nonionic detergent) from Nikko Chemicals Co., Ltd., Tokyo, Japan. Triton X-100 was obtained from Boehringer Mannheim GmbH. N-ethylmaleimide was obtained from Calbiochem Behring Corp., Calif.

Starting plasmids were: Plasmid pU6 containing coding regions for CH3, CH4 and M of murine IgM heavy chain cloned into the PstI site of pBR322 (Rogers et al., *Cell* (1980) 20:303-312); plasmid pG2, derived from pMC18; plasmid pMC18 contains cDNA for a chimpanzee α-globin cloned into the PstI site of pBR322, where pG2 was generated by digesting pMC18 with EcoRI, filling in the sole EcoRI site with the Klenow fragment of DNA polymerase I ("pol I K") and religation, where the abolished EcoRI site resulted in an XmnI site; plasmid pPB920B contains a single EcoRI site, as well as both ampicillin and kanamycin resistant genes; plasmid pGM/N1 was derived from pG2 by deletion of lactamase coding regions and placement of an EcoRI linker at the formerly NcoI site of globin.

The structure of pMC18 and deletion plasmid is shown in FIG. 1. Plasmid pMC18 shows the β-lactamase gene (dots) interrupted by a chimpanzee α-globin cDNA sequence (white). The β-lactamase signal sequence is indicated (black). The horizontal arrows indicate the steps involved in constructing pGM/N1 in which all but the two amino terminal codons of the β-lactamase signal sequence are deleted. The EcoRI site was filled in to generate an XmnI site by sequential treatment with EcoRI, pol I K plus dXTP's, then T4 ligase.

The resulting plasmid pG2 was linearized with MboII in the presence of 5 μg/ml of ethidium bromide, and treated with NcoI which cuts at the start codon of the α-globin gene. After treatment with pol I K, the terminus generated at the MboII site following the first two codons of the β-lactamase gene was fused to the NcoI generated terminus at the start codons of globin with an intervening EcoRI 12 bp linker (see below).

Figure 2:
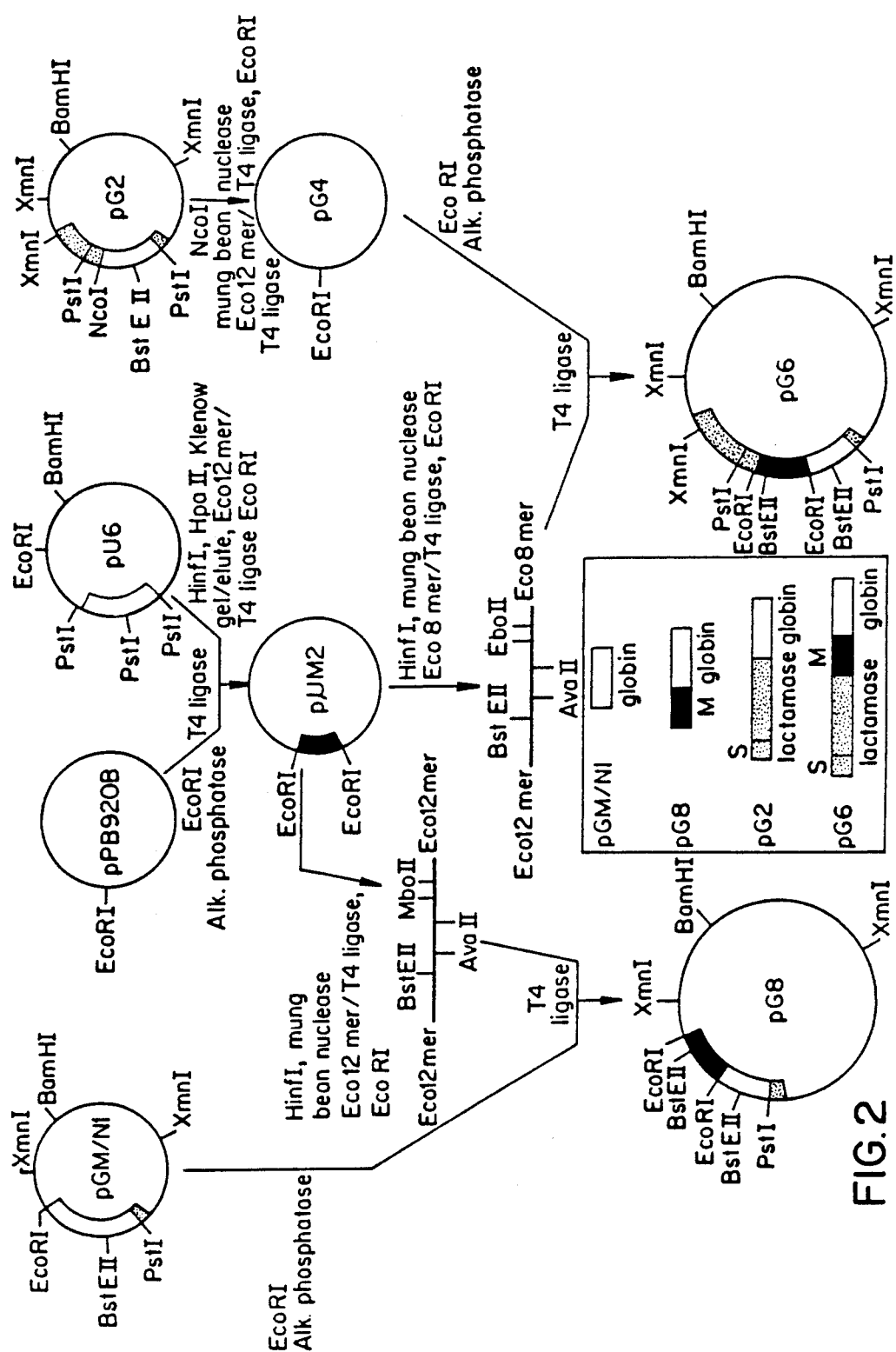
FIG. 2 is a flow diagram of plasmids pG6 and pG8 having constructs with and without start transfer signals, respectively.

As shown in FIG. 2, a 200 bp fragment including all of the M coding sequence (transmembrane integrator sequence) was excised from pU6 by digestion with HinfI and HpaII, followed by filling in with pol I K and purification by gel electrophoresis followed by elution A linker (12mer) having an EcoRI site and the following formula:

5' C C G G A A T T C C G G 3'
    G G C C T T A A G G C C was ligated employing T4 ligase, followed by restriction with EcoRI. The EcoRI-EcoRI fragment was cloned into pPB920B.

This cloned fragment was modified as needed after HinfI digestion, by treatment with mung bean nuclease in order to destroy the termination codon, followed by ligation to EcoRI 8- or 12mer linkers in order to maintain correct reading frame into globin in either pG2 (EcoRI 8mer) or pGM/N1 (EcoRI 12mer). The mer had the following formula:

5' G G A A T T C C 3'
    C C T T A A G G

The modified EcoRI tailed fragment was now ready for use.

Plasmid pG2 was modified to convert the sole NcoI site at the 5' end of the globin coding sequence into an EcoRI site by cleavage with NcoI, removal of single strands with mung bean nuclease and ligation to EcoRI 12mer linkers (see above), recleaving with EcoRI and religating with T4 DNA ligase. The resulting plasmid was called pG4.

The 200 bp M encoding fragment was cloned into pG4 and pGM/N1 by restriction of pG4 and pGM/N1 with EcoRI, followed by hydrolysis of terminal phosphate with alkaline phosphatase. After ligating with T4 ligase, plasmids pG6 and pG8 were obtained, respectively. Tet resistant transformants were screened for correct orientation by BamHI-BstEII digests. Two μg of each plasmid, pG8, pG6, pG4, pG2 and pGM/N1 were digested in a total volume of 20 μL with restriction endonucleases BamHI and BstEII at 37° C. exhaustively. Digestion products were analyzed by gel electrophoresis in 6% polyacrylamide gels (In FIG. 2, S refers to the signal sequence and M refers to the M segment.)

The approximately 200 bp M segment coding fragment derived from murine IgM heavy chain contains no BamHI site and only a single BstEII site, approximately 50 bp in from the 5'-end of the coding region, while both parent plasmids contain a single BamHI site and a single BstEII site, the former in the tetracycline resistance gene and the latter in the middle of the globin coding sequence A comparison of the BamHI-PstEII digests show insertion of the M coding fragment in correct orientation resulting in a new approximately 450 bp BstEII-BstEII fragment in plasmids pG6 and pG8 constructed respectively from pG2 and pGM/N1. As expected, the BamHI-BstEII fragment of parent pG2 is approximately 500 bp larger than that of parent pGM/N1, whose lactamase coding region has been deleted. The BamHI-BstEII fragment from pG4 is identical in size to that of pG2.

For transcription of pG6 and pG2, plasmid DNA (4 μg) was added to transcription reactions of 20 μl using conditions essentially identical to that described by Roberts et al., *Proc. Natl. Acad. Sci. USA* (1978) 75:1485–1489. The reactions were supplemented with human placental ribonuclease inhibitor. Transcription was carried out for 10 min. at 37° C. and transferred immediately to ice. Aliquots (4 μl) were added to wheat germ translation reactions with magnesium and potassium readjusted to optimize for translation (2 mM Mg and 140 mM KOAc). Translation incubations were at 27° C. for 90 min. Dog pancreas microsomal membranes (5 $A_{260}$ units/ml) were present in some of the translation reactions (+membranes) or were added post-translationally in the case of other reactions (pt membranes). In some cases trypsin was added to a final concentration of 0.1 mg/ml for 1 hr at 23° C. and protease digestion was terminated with 1 mM phenylmethylsulfonyl fluoride and 1% Trasylol, followed by ice cold 15% trichloroacetic acid. Some reactions received in addition 1% Triton X-100. All reactions were subjected to immunoprecipitation with either anti-lactamase anti-serum or anti-α-globin serum or non-immune serum.

Based on the determination of the approximate molecular weight of the proteins formed under the conditions described above, the following conclusions were drawn. The lactamase globin fusion protein encoded by pG2 is completely translocated across the microsomal membranes as evidenced by co-translational processing to a form termed G2 and by protection from trypsin in 27e absence of added detergents to solubilize the protecting lipid bilayer.

Plasmid pG6 which contained the M segment coding region inserted just 5' to the globin codons programs the synthesis of a correspondingly higher molecular weight (42 kdal) lactamase and globin immunoreactive polypeptide termed pre G6. This nascent chain was also processed by added microsomal vesicles, retaining both globin and lactamase immunoreactivity. Digestion with trypsin post-translationally resulted in a shift down to a 28 kdal major band as predicted for the molecular weight of the lactamase and transmembrane segment domains alone. This band, termed G6', which did not appear upon protease digestion in the absence of microsomal membranes or after their addition post-translationally, was immunoreactive to anti-lactamase, but not to anti-α-globin antisera.

When non-ionic detergents were used to solubilize the protecting lipid bylayer, both the protected lactamase domain of pG6 and the entire protected lactamase globin fusion of pG2 were totally destroyed by the added proteases.

These results were consistent with the predicted behavior of a stop transfer sequence converting the secreted fusion protein into a transmembrane protein asymmetrically oriented with lactamase and globin domains on opposite sides of the membrane.

These conclusions were further confirmed by extraction experiments using sodium carbonate at pH 11.5. Under these conditions (Fugiki et al., *J. Cell Biology* (1982) 93:97), membrane vesicles are converted into sheets and peripheral and content proteins (internal to vesicles) can be separated from integral membrane proteins by sedimentation. It was found that G6 was quantitatively retained in the pellet, but that G2 and residual pre G2 and pre G6 were largely extracted into the supernatant.

Following the above procedure, transcription and translation reactions were carried out using plasmid DNA of pG8. The parent plasmid for this construction, pGM/N1, encodes a fusion protein termed GM/N1, the bulk of whose lactamase and signal coding regions have been deleted, resulting in a cytosolic protein beginning with the initial methionine and serine of lactamase, followed by an EcoRI linker and the entire coding region of α-globin. The EcoRI tailed M segment coding region was inserted into the EcoRI site in correct orientation. This plasmid, pG8, encoded a fusion protein called G8, which was found to be neither processed nor protected from proteases after co-translational addition of microsomal membranes.

Example II

Materials and Methods

Materials: All restriction endonucleases, nuclease Bal 31, calf intestinal alkaline phosphatase, SP6 RNA polymerase, T4 DNA ligase, and Klenow fragment of *E. coli* DNA polymerase were from Boehringer Mannheim Diagnostics, Inc., Houston, Tex. or from New England BioLabs, Beverly, Mass. RNase inhibitor was from Promega Biotec, Madison Wis.; staphylococcal protein A-Sepharose was from Pharmacia, Inc., Piscataway, N.J.; rabbit antihuman globin serum was from Cappel Laboratories, Cochranville, Pa.; rabbit anti-ovine prolactin was from United States Biochemical Corp., Cleveland, Ohio; proteinase K was obtained from Merck, FRG; endoglycosidase H (Endo H) and [$^{35}$S]-methionine (translation grade, >800 Ci/mmol) were from New England Nuclear, Boston, Mass; Nikkol (octa-ethleneglycol-mono-n-dodecyl ether, a non-ionic detergent) was from Nikko Chemicals, Co., Ltd., Tokyo, Japan. Plasmid pSBBP3 was constructed by William Hansen, Department of Biochemistry and Biophysics, University of California at San Francisco, using bovine preprolactin cDNA (Isasavago et al. (1982) *J. Biol. Chem.* 257:678–681). All globin encoding plasmids were derived from pMC18 (Yost et al. (1984) *Cell* 34:759–766).

Plasmid pSPBP3, containing the entire coding region for bovine preprolactin, was linearized with NcoI in the presence of ethidium bromide and the overhang filled in by treatment with *E. coli* DNA polymerase I Klenow fragment in the presence of all four dNTPs. The plasmid was then cut with PstI and the 850-base pair (bp) fragment containing the preprolactin coding region was purified on, and eluted from, a 1% low melting point agarose gel. Plasmid pSPG1E was cut with BstEII, the 5' overhang filled in as described above, then cut with PstI and the 3-kilobase (kb) vector gel purified. The purified pSPBP3 fragment and pSPG1E vecter were treated with T4 DNA ligase. After transformation of *E. coli*, plasmid DNA was prepared from individual ampicillin-resistant colonies and screened by restriction enzyme analysis with NcoI and Sph1 for appropriate sized fragments.

To introduce an N-linked glycosylation site into the globin domain of pSPGP1 plasmid pSPSG1 was used, an exact fusion of the β-lactamase signal sequence and chimpanzee α-globin in which a synthetic oligonucleotide encoding Ala-His-Asn-Gly-Ser-Gly-Ser-Gly had been inserted into the BssHII site of the globin coding region. The translation product of this plasmid is translocated across the ER membrane and is core glycosylated in vitro. The region encoding the β-lactamase signal sequence was deleted by digestion with NcoI and BglII, treated with Klenow fragment to fill in the 5' overhangs, and recircularized with T4 ligase. The resulting plasmids were used to transform *E. coli*, and plasmid DNA was prepared from individual ampicillin-resistant colonies and screened by restriction enzyme analysis with HindIII. The 430-bp HindIII fragment of the positive clone, pSPSG3, was inserted into pSPGP1 which had been digested to completion with HindIII and treated with calf intestinal alkaline phosphatase to prevent self-ligation. *E. coli* were transformed and DNA prepared from individual ampicillin-resistant colonies was screened with NcoI to determine the presence and correct orientation of the HindIII insert.

SP6 plasmids were transcribed in vitro (Kreig and Melton (1983) *Nucleic Acids Res.* 12:7057–7070) at a concentration of 0.2 mg/ml in a reaction mix containing 40 mM Tris-HCl pH 7.5, 6 mM MgCl$_2$, 2 mM spermidine, 10 mM dithiothreitol, 25 µg/ml calf-liver tRNA, 0.5 mM each ATP, CTP and UTP, 0.1 mM GTP, 0.5 mM GpppG, 0.9 U/µl RNase inhibitor, and 0.4 U/µ SP6 RNA polymerase. Reactions were carried out at 40° C. for 1 h and aliquots used directly in transcription-linked translations in the rabbit reticulocyte lysate cell-free system at a concentration of 20%. Translation reactions were carried out in 20–200 µl vol. that contained 43% rabbit reticulocyte lysate (Merrick (1983) *Methods Enzymol.* 101:606), 100 mM KCl, 2 mM MgCl$_2$, 0.9 mM ATP, 10 mM creatine phosphate, 0.1 mM each of 19 amino acids minus methionine, 16 mM Tris HCl (pH 7.5), 0.44 mM spermidine, 2 mM dithiothreitol, 0.4 mg/ml creatine phosphokinase, 0.1 mg/ml calf-liver tRNA, and 1 mCi/ml [$^{35}$S]methionine. Reaction mixtures were incubated at 24° C. for 60 min.

In vitro transcripts of SP6 plasmids were translated separately in a rabbit reticulocyte cell-free system in the presence or absence of intact dog pancreas rough microsomes (Blobbel and Doberstein (1975) *J. Cell Biol.* 67:852–862). Translation products were immunoprecipitated and separated by SDS PAGE. Bands were localized by autoradiography and quantitated by densitometer scanning of preflashed film using an LKB 2202 Ultroscan Laser Densitometer from LKB Instruments, Inc., Gaithersburg, Md.

To determine percentage processing of pSPGP1 translation products in vitro, translation reactions were carried out in the presence of varying membrane concentrations (0, 1.25, 2.5 or 5.0 A$_{280}$ U/ml). Reactions were stopped after 1 h at 24° C. by chilling on ice. Samples were split in half 5 µl each) and immunoprecipitated with either globin or prolactin antiserum. Samples were prepared and subjected to SDS PAGE (Blobbel and Doberstein, 1975, supra). The intensities of preGSP, GS1 and P1 bands were quantitated by densitometry. Percentage processing of preGSP to GS1 was determined by [GS1×11/4]/preGSP+(GS1×11/4]×100 and processing to P1 by [(P1×11/7)/preGSP (P1×11/7)]×100 to compensate for the differential methionine contents of the three proteins (preGSP contains eleven, P1 seven, and GS four).

Translocation of preGSP and its cleavage products, GS1 and P1, across microsomal membranes was determined by two independent methods: (a) sensitivity of translation products to protease digestion and (b) addition of carbohydrate to the Asn-X-Ser N-linked glycosylation site engineered into the globin coding region.

Protease protection experiments were done as follows after 1 h at 24° C., translation reaction mixtures were chilled on ice, adjusted to 10 mM $CaCl_2$, and divided into equal aliquots of 5 or 10 μl. Some were treated with proteinase K (dissolved in 10 mM $CaCl_2$, 50 mM Tris pH 7.5 and preincubated at 37° C. for 15 min) at a final concentration of 0.1–0.4 mg/ml either in the presence or absence of 1% Nikkol (a nonionic detergent used to disrupt the lipid bilayer). All samples were incubated at 0° C. for 1 hr. Proteinase digestion was stopped by the addition of 2 mM phenylmethylsulfonyl fluoride and immediately transferred to 4–5 volume 1% SDS, 0.1 M Tris-HCl, pH 8.9, preheated to 100° C., then incubated at 100° C. for 10–15 min. Samples were diluted 20-fold in a solution of 1% Triton X-100, 0.1 M Tris, pH 8.0, 10 mM EDTA, 100 mM NaCl, subjected to immunoprecipitation with either 0.5 μl anti-prolactin antiserum or 4 μl anti-globin antiserum, and protein A-Sepharose-CL4B, followed by SDS-PAGE. Bands were viewed by autoradiography and quantitated by densitometric scanning. Percentage protection was determined for all bands by [band (+protease)/band (−protease)]×100.

Endo H digestion was used to determine core glycosylation of translation products. Endo H removes simple N-linked carbohydrates, causing a shift to a lower apparent molecular weight upon SDS-PAGE. Translation products of pSPgGP1 obtained in the presence or absence of membranes were immunoprecipitated and eluted in 100 μl 0.1 M sodium citrate pH 5.5, 0.1% SDS. Samples were heated to 100° C. for 2 min, supernates removed and divided into two aliquots. Endo H was added to one aliquot to a final concentration of 1 pg/ml, and both aliquots incubated at 37° C. for 12 h. After digestion, 10 μg of carrier bovine serum albumin (BSA) was added, and samples were chilled and adjusted to 15% ice-cold trichloroacetic acid, precipitates collected by centrifugation, and samples prepared for SDS PAGE as usual.

Translation products (10 μl) obtained in the presence of 4 $A_{280}$ U/ml dog pancreas rough microsomes were diluted 250-fold (to 2.5 ml) with either ice-cold 0.1 M sodium carbonate pH 11.5 (Blobbel and Dobbins, 1975, supra) or ice-cold 0.25 M sucrose, 5 mM $MgCl_2$, 1 mM dithiothreitol, 50 mM triethanolamine, pH 7.4, 0.1 M KCl and incubated at 0° C. for 30 min. The samples were centrifuged at 0° C. for 1 h at 50,000 rpm in polycarbonate tubes in a Beckman 70.1 Ti rotor (Beckman Instruments, Inc., Palo Alto, Calif.). The supernatants were removed, the sides of the tube carefully dried with a Kimwipe, and the membrane pellets dissolved in a 1% Triton X-100 buffer 0.1 M Tris-HCl pH 8.3, 10 mM EDTA, 100 mM NaCl, 1 mM PMSF. The pH of the carbonate samples was adjusted to 7–7.5 with acetic acid, and all samples were immunoprecipitated with either antiprolactin or anti-globin serum, prepared and subjected to SDS-PAGE and autoradiography.

Upon expression in a transcription-coupled rabbit reticulocyte lysate cell-free translation system, pSPGP1 encoded a fusion protein of −32 kD with both globin and prolactin immunoreactivity called preGSP. When translation reactions were supplemented with microsomal membranes two additional translation products, not present in the absence of membranes, were seen after electrophoresis on polyacrylamide gels in SDS with subsequent autoradiography. One of these bands, termed P1, was found to be anti-prolactin but not anti-globin immunoreactive and to co-migrate with authentic mature bovine prolactin. The other product, termed GS1, was anti-globin but not anti-prolactin immunoreactive, and migrated with an apparent molecular weight slightly greater than that of authentic full-length globin. When membranes were added after completion of protein synthesis with further incubation, neither of these bands were generated. The difference in the relative intensities of the bands in the autoradiographs is due to the methionine distribution in the [$^{35}$S]methionine-labeled, newly synthesized proteins. Upon processing, of the eleven methionines in preGSP, P1 contains seven and GS1 only four.

When membranes were present during translation, GS1 and P1 were generated in a 1:1 ratio and the percentage processing of both products increased correspondingly with membrane concentration. These data indicate that GS1 and P1 are generated from a common (nascent) precursor and that the processing activity is associated with the microsomes.

The results indicate that the prolactin signal sequence, now localized internally, is still functional as evidenced by accessibility of the signal sequence cleavage site to signal peptidase, a lumenally disposed enzyme of the endoplasmic reticulum. The products of this cleavage are authentic prolactin (P1) and globin with the prolactin signal sequence attached at its carboxy terminus (GS1).

The HindIII fragment of this plasmid (lacking a signal sequence but containing an N-linked glycosylation site engineered into the BssH II site) was excised and ligated in place of the corresponding HindIII fragment of pSPGP1 (which lacked the glycosylation addition site). The resulting construction, pSPgP1, differed from pSPGP1 only in the presence of the 24-bp oligonucleotide encoding a glycosylation addition site, and the encoded proteins are identical except for the insertion of eight amino acids, Ala-His-Asn-Gly-Ser-Gly-Ser-Gly, between amino acids 20 (Gly) and 21 (Ala) in the globin domain of the pSPgGP1 gene product. Since glycosylation is restricted to the lumen of the ER, addition of N-linked sugars represents a definitive assay for translocation that is independent of other criteria such as protection from proteolysis or signal peptide cleavage.

When pSPgGP1 is transcribed and translated as described previously for pSPGP1, a −32-kD globin and prolactin immunoreactive protein was synthesized. The co-translational (but not posttranslational) addition of microsomal membranes resulted in appearance not only of the 26-kD P1 band and the 14-kD gGS1 band, analogous to GS1 in the presence of pSPGP1, but also in the appearance of a 16-kD globin but not prolactin immunoreactive band. This new 16-kD band, termed gGS1', appears to be the glycosylated derivative of gGS1. Consistent with this interpretation, gGS1' was well protected from proteases, as was P1, while gGS1 was relatively poorly protected. Protection of gGS1 approximated that of GS1 (20%), presumably representing those chains of gGS1 that were translocated but not glycosylated, an intermediate often observed in glycoprotein biosynthesis in vitro and in vivo. Also, as was seen with preGSP, the precursor, pre-gGSP, was not protected.

Treatment with Endo H shifted the position of gGS1' on SDS-PAGE to that of gGS1, thereby demonstrating the presence of carbohydrate on gGS1'. Similar treatment of the protein encoded by pSPSG3, which contains the glycosylation site but lacks a signal sequence to allow its utilization, demonstrates neither shift up on SDS-PAGE with co-translational membranes, nor protection from proteolysis, nor shift down with Endo H digestion.

Sedimentation of membranes in either isotonic sucrose buffer or after extraction with sodium carbonate, pH 11.5, a procedure designed to strip off nonintegral proteins and content proteins from microsomal membranes, resulted in all forms (preGSP, gGS1, gGS1', and P1) being extracted by carbonate and both P1 and gGS1' sedimented quantitatively with membranes in sucrose buffer. Control extractions with a translation product known to integrate into membranes co-translationally demonstrated the fidelity of carbonate extraction. Both gGS1 and pre-gGSP were found in both the supernate and the pellet after membrane sedimentation in sucrose. The majority of gGS1 was sedimented with microsomes, while pre-gGSSP was split approximately evenly between the membrane pellet and the supernate.

These data indicate that gGS1' is not integrated into the vesicle membrane but exists either free in the microsomal lumen or peripherally associated with membrane proteins of the vesicle lumen. Also, those chains of gGS1 that are not protected from proteolysis are apparently in large measure bound to the membranes.

Constructions

Recombinant DNA constructs were derived from existing plasmids, pG6 (Yost et al. (1983) *Cell* 34:759–766), and pSPgGSP (previously termed pSPgGP1, Perara and Lingappa (1985) *J. Cell Bio.* 101:2292–2301). pG6 was modified by EcoRI/BstEII elimination of 50 base-pairs, followed by insertion of an NcoI linker (GCCATGGC), leaving 50 base pairs coding for the carboxy terminus of membrane μ heavy chain. The entire coding region was engineered behind the SP6 promoter. Thus, this pG6 derived construct, pSPSLMG, includes coding regions for: lactamase with its signal sequence (182 codons); the transmembrane region of IgM (M segment, 50 codons); and chimpanzee β-globin (143 codons). The plasmid pSPLM was constructed by truncation of the globin of pSPSLMG at BstEII and in the SP64 polylinker at XbaI with religation, followed by partial digestion of pSPSLMG with SspI in the presence of ethidium bromide followed by Bal 31 digestion, repair with Klenow fragment, and religation. This eliminated the initial methionine, and with immunoprecipitation, mobility of translation products on SDS-PAGE are consistent with initiation of synthesis at amino acid number 66, which is the next methionine of lactamase. Plasmid pSPLMG thus encodes amino acids 66 through 182 of lactamase (without its signal sequence), 50 amino acids of M segment, and the first 110 codons of globin, ending at BstEII.

Plasmid pSPgGMP was constructed from pSPgSGP by insertion of the M segment at the BstEII/NcoI site of pSPgGSP preceding the coding region for the prolactin signal. Subcloning was followed by deletion of the prolactin signal by cleavage at the EcoRI site at the distal end of the M segment and at the PvuII site 50 codons beyond the amino terminus of mature prolactin. Religation yielded pSPgGMP which encodes: the first 110 amino acids of chimpanzee β-globin, including a 7 amino acid glycosylation site at the prolactin signal. Subcloning was followed by deletion of the prolactin signal by cleavage at the EcoRI site at the distal end of the M segment and at the PvuII site 50 codons beyond the amino terminus of mature prolactin. Religation yielded pSPgGMP which encodes: the first 110 amino acids of chimpanzee β-globin, including a 7 amino acid glycosylation site at the BssHII of globin; the 50 amino acid M segment and the C terminal 150 codons of mature prolactin. The parent plasmid, pSPgGSP, encodes the same 117 amino acids of globin (with the glycosylation site), fused to the signal of prolactin (30 codons) and all 199 codons of mature prolactin. The coding regions of the four constructs are diagrammed in FIG. 3.

Transcription-Linked Translation

Transcription of SP6 plasmids was as described previously (Perara and Lingappa, 1985, supra). Aliquots of the transcription reaction mixture were used directly in transcription-linked translations at a final concentration of 20%. Translation reactions of this kind in reticulocyte lysate have already been described (Perara and Lingappa, 1985, supra). Translations in wheat germ extract were essentially as described (Erickson and Blobel (1983) *Methods Enzymol.* 96:38–50), except that the final ion concentrations were maintained at 2.6 mM magnesium and 140 mM potassium and the pH was adjusted to 7.5 using Tris base. Reaction mixtures were incubated at 24° C. for 60 min. Some translations were supplemented either with dog pancreas microsomes or salt extracted (signal recognition particle (SRP) depleted) microsomes. Microsomal membranes were prepared as described (Walter an Blobel (1983) *Methods Enzymol.* 96:84–93) except that the column washing step was replaced by two consecutive washes of the membranes by pelleting (30 min, 100,000×g) and resuspending of the membranes in 50 mM triethanolamine (TEA), 1.5 mM Mg(OAc), 1 mM EDTA, 1 mM dithiothreitol (DTT), 0.5 mM phenylmethylsulfonyl fluoride (PMSF). SRP was prepared from these membranes as described (Walter and Blobel (1983) *Methods Enzymol.* 96:682–691) except that the final sucrose gradient centrifugation step was omitted. Ion concentration for each column fraction was estimated from the measured conductance.

Protein Processing and Translocation Assays

In vitro translation products were immunoprecipitated and separated by SDS PAGE. Bands were localized by autoradiography either with or without fluorography. Protease protection experiments were performed as described (Perara and Lingappa, 1985, supra), except for wheat germ products where digestion was allowed to proceed for 1 h at 20° C. and microsomes were solubilized with Triton X-100 (0.1% final concentration) instead of Nikkol.

To determine the extent of SRP arrest for each of the plasmids, translations were carried out with and without SRP. Total products were separated by SDS PAGE and localized by autoradiography without fluorography. Bands were quantitated by densitometer, scanning the autoradiographs using an LKB 2222 Ultrascan XL Laser Densitometer from LKB Instruments, Inc., Gaithersburg, Md. To facilitate integration, peaks were smoothed by convolution with a Guassian filter In each case translation in the absence of SRP was normalized to 1.0 integrated OD units.

NEM Treatment of Microsomal Membranes

Salt washed microsomal membranes were prepared (Walter and Blobel, 1983, supra). A 10 μl aliquot at 50 A280 U/ml was adjusted to 50 mM N-ethyl maleimide (NEM) by addition of 1 μl volume of 50 mM NEM freshly prepared in 10 mM Tris pH 8 and incubated at 22° C. for 15 min and at 4° C. for 30 min. The reaction was quenched by adjusting the aliquot to 10 mM DTT by addition of 0.5 μl of 0.1 M DTT in water and further incubation at 4° C. for 30 min. Mock NEM treated membranes were prepared by premixing 1 μl of 50 mM NEM in 10 mM Tris, pH 8 with 0.5 pl 0.1 M DTT in water and then adding 10 μl of salt washed membranes followed by sequential incubations for 15 min at 22° C. and 1 h at 4° C.

Figure 3:
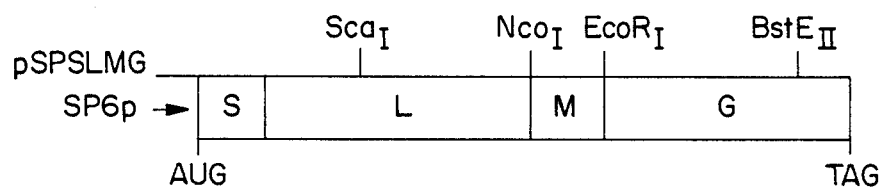
FIG. 3 is a diagram of the coding regions of plasmids of pSPSLMG, pSPLMG, pSPgGSP and pSPgGMP.
Figure 3:
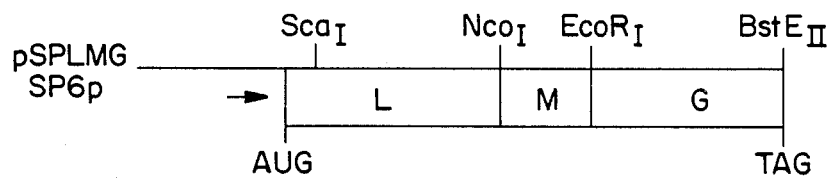
Figure 3:
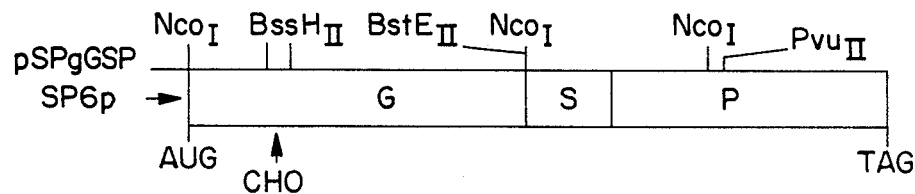
Figure 3:
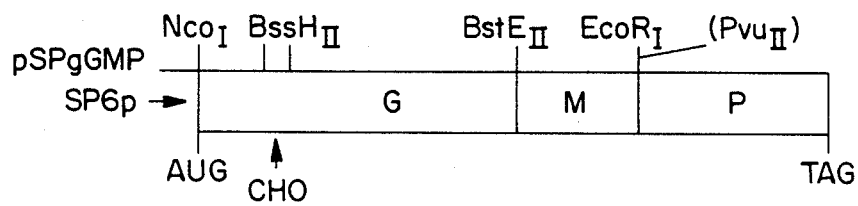

Plasmid pSPSLMG, diagrammed in FIG. 3, encodes sequentially and in frame, a signal sequence (S) followed by a domain of lactamase (L), a stop transfer sequence (M) and finally, globin (G). When pSPSLMG is expressed in the reticulocyte lysate cell-free protein synthesizing system in the presence of microsomal membranes a new product of lower molecular weight, approximately 26 kd, that was lactamase but not globin immunoreactive was obtained. Therefore LMG must span the bilayer asymmetrically with the 26 kd lactamase-M domain in the vesicle lumen and the 14 kd globin domain exposed on the cytoplasmic face. This result is consistent with expectation from work on a related coding region (Yost et al. (1983) *Cell* 34:759-766).

To study the behavior of the M segment alone without a preceding signal sequence, a deletion mutant of pSPSLMG, termed pSPLMG, was constructed, in which the signal codons (as well as a few codons from the amino and carboxy termini of authentic lactamase and globin, respectively), were removed. In the encoded product, a 34 kd polypeptide called LMG*, the M segment is flanked by the in-frame sequences of lactamase and globin. Both the lactamase and globin domains of this protein appeared to be translocated across the membrane. Translocation was inferred from the detection of both lactamase and globin immunoreactivity protected from proteinase K in the form of two discrete fragments of approximately 19 and 15 kd termed L* and G*, respectively, generated by cleavage of full length LMG*. While both of the flanking domains were translocated, the stop transfer sequence containing M segment itself was not, since proteolytic digestion of LMG* resulted in cleavage into the two protected products. Each of the protected domains was slightly larger than expected for the authentic lactamase and globin regions, presumably due to a small remnant of the M segment on each.

In order to directly compare the signal-like function of M to that of a conventional signal sequence pSPgGMP was constructed from plasmid pSPgGSP. Plasmid pSPgGMP contains the M coding region engineered between two flanking coding regions (117 residues of globin including an artificially engineered glycosylation site and 150 residues of bovine prolactin). By comparison, plasmid pSPgGSP encodes a fusion protein that contains the same 117 residues of chimpanzee globin followed by the signal sequence of bovine prolactin which is followed by the entire authentic prolactin coding region. Thus, pSPgGMP and pSPgGSP differ in that the former contains an internal stop transfer sequence while the latter contains an internal signal sequence. An additional difference, the lack of 50 authentic prolactin codons in pSPgGMP, is insignificant since expression of a similar deletion from pSPGSP, in a plasmid called pSPgGSPK1, demonstrates similar translocation behavior.

It has been shown that the former amino terminal signal sequence of bovine prolactin, when engineered to the internal position in pSPgGSP, is still capable of functional recognition of translocation receptors on the ER membrane, in an obligate co-translational fashion (Perara and Lingappa, 1985, supra). The nascent protein termed GSP, encoded by pSPgGSP, was shown to interact productively with receptors for translocation on the ER membrane. Cleavage of the signal sequence resulted in the generation of three fragments, GS, gGS and P. The former two comprise the unglycosylated and glycosylated globin domains attached to the cleaved signal peptide, the latter fragment is mature bovine prolactin. All fragments were translocated across membranes as indicated by protection from proteinase K digestion. Moreover, the signal sequence was not buried in the lipid bilayer, but rather, was itself translocated to the vesicle lumen, as shown by carbonate extraction.

The presence of similar flanking domains in pSPgGSP and pSPgGMP facilitates comparison of the "signal-like" behavior of the M segment stop transfer sequence with that of the prolactin signal sequence. Expression of pSPgGMP in the absence of membranes results in synthesis of a protein called GMP*. When membranes are present co-translationally, but not when added after completion of protein synthesis, a fraction of nascent GMP* is glycosylated, gGMP*. Proteinase K digestion of translation products synthesized in the absence of membranes or with membranes added post-translationally results in no protease protected fragments. However, when membranes were present during translation, subsequent proteolysis generated discrete protected fragments corresponding to the globin and prolactin domains. Two fragments immunoreactive with anti-globin serum were observed and appear to correspond to glycosylated and non-glycosylated forms of globin containing a small remnant of M. One fragment was found to be immunoreactive with anti-prolactin and corresponds in size to that expected for the prolactin domain together with a part of the M segment. Thus, when expressed in the reticulocyte lysate cell-free system, pSPgGMP was found to translocate both flanking domains with glycosylation of the globin moiety. However, in contrast to the signal sequence of pSPGSP, the stop transfer sequence of pSPGMP was not itself translocated, as demonstrated by its accessibility to digestion by proteinase K.

It is evident from the above results, that novel products can be prepared having unique properties and capabilities. In accordance with the subject invention, cells can be modified so as to have membrane bound proteins either or both intracellular or extracellular, which proteins are either exogenous to the cell or provide for enhanced amounts of a particular endogenous protein associated with an oligopeptide different from the natural protein. By virtue of this novel capability, one can enhance or provide for the processing of excreted or secreted proteins, by providing for peptidases being bound to the membrane. In addition, one can provide for novel markers on the surface of a cell, whereby the cell can be used as a particle for binding to other cells or receptors, can be used as a label, for example, where the cell is an erythrocyte, can provide for modified histocompatibility antigens, where the cell is prokaryotic, can provide for novel vaccines, or the like. Furthermore, novel receptors can be provided, which can be used to activate processes internal to the cell, where the cell lacks such receptors or its receptors are malfunctioning.

Although the foregoing invention has been described in some detail by way of illustration and example for purposes of clarity of understanding, it will be obvious that certain changes and modifications may be practiced within the scope of the appended claims.

What is claimed is:

1. A method for modifying a plasma or microsomal membrane by genetically programming the binding of a polypeptide non-covalently to a cellular lipid membrane capable of translocating a nascent poly(amino acid) comprising at least one open reading frame joined to a transmembrane integrator sequence (tmi), said method comprising:

combining (1) a DNA sequence comprising in reading frame a tmi from a surface immunoglobulin and flanked on both sides by open reading frames encoding polypeptides in reading frame with said tmi, wherein said open reading frames are not naturally joined to said tmi, and flanking DNA sequences comprising transcriptional and translational initiation and termination regulatory signals; (2) cellular membrane; and (3) translational components, to provide an expression system; and incubating said expression system, whereby said DNA sequence is translated to said poly(amino acid) and said poly(amino acid) is translocated to said membrane and becomes bound to said membrane.

2. A method according to claim 1, wherein said combining is by means of transforming a host cell with said DNA sequence, wherein said transcriptional and translational regulatory signals are functional in said host cell.

3. A method according to claim 2, wherein said host cell is prokaryote.

4. A method according to claim 2, wherein said host cell is eukaryote.

5. A method for modifying a plasma or microsomal membrane by genetically programming the binding of a polypeptide non-covalently to a cellular lipid membrane capable of translocating a nascent poly(amino acid) comprising at least one open reading frame joined to a transmembrane integrator sequence (tmi), said method comprising:

combining (1) a DNA sequence comprising in reading frame a tmi from a surface immunoglobulin, a signal sequence upstream from and in reading frame with said tmi and flanking open reading frames encoding polypeptides in reading frame with said tmi and said signal sequence and one of said open reading frames linking said signal sequence with said tmi, wherein said open reading frames are not naturally joined to said tmi, and flanking DNA sequences comprising transcriptional and translational initiation and termination regulatory signals; (2) cellular membrane; and (3) translational components, to provide an expression system; and incubating said expression system, whereby said DNA sequence is expressed to produce said poly(amino acid) and said poly(amino acid) is translocated to said membrane and becomes bound to said membrane.

6. A method according to claim 5, wherein said signal sequence is at the 5'-terminus of said DNA sequence.

7. A method according to claim 5, wherein said tmi has an open reading frame downstream from said tmi.

8. A method according to any of claims 5, 6 or 7, wherein said combining is by means of transforming a host cell with said DNA sequence, wherein said transcriptional and translational regulatory signals are functional in said host cell.

9. A method according to claim 8, wherein said host cell is a prokaryote.

10. A method according to claim 8, wherein said host cell is a eukaryote.

11. A method according to claim 6 wherein said immunoglobulin heavy chain is the mu chain.

12. A method according to claim 5, wherein said signal sequence is joined to a second open reading frame located adjacently and 5' to said signal sequence.

13. A DNA sequence comprising a signal sequence and a transmembrane integrator sequence (tmi) of surface immunoglobulin, wherein the tmi is joined to an open reading frame in reading phase with said open reading frame, wherein said reading frame is other than the naturally occurring contiguous open reading frame.

14. A DNA sequence comprising a transmembrane integrator sequence of surface immunoglobulin flanked in proper reading frame with a 5'-sequence encoding a polypeptide lacking a signal sequence and a 3'-sequence encoding a polypeptide, wherein at least one of said flanking sequences is other than the sequence naturally joined to said tmi.

15. A DNA sequence according to any of claims 13 or 14, wherein said DNA sequence is flanked by transcriptional and translational regulatory signals and is under their regulatory control.

16. A DNA sequence according to claim 15, wherein said transcriptional and translational regulatory signals are eukaryotic signals.

17. A vector capable of extrachromosomal maintenance comprising a DNA sequence according to claim 15.

18. A prokayotic vector capable of extrachromosomal maintenance comprising a DNA sequence according to claim 15.

19. A eukaryotic cell comprising a DNA sequence according to any of claims 13 or 14, wherein said DNA sequence is flanked by transcriptional and translational regulator signals functional in said eukaryotic cell and is under their regulatory control.

* * * * *